(12) United States Patent
Leary et al.

(10) Patent No.: US 7,375,188 B2
(45) Date of Patent: May 20, 2008

(54) VEGETARIAN PROTEIN A PREPARATION AND METHODS THEREOF

(75) Inventors: Thomas Richard Leary, Shoreline, WA (US); Daniel Lafoe, Bothell, WA (US)

(73) Assignee: Mallinckrodt Baker, Inc., Phillipsburg, NJ (US)

( * ) Notice: Subject to any disclaimer, the term of this patent is extended or adjusted under 35 U.S.C. 154(b) by 0 days.

(21) Appl. No.: 11/194,093

(22) Filed: Jul. 29, 2005

(65) Prior Publication Data

US 2007/0026489 A1 Feb. 1, 2007

(51) Int. Cl.
*C07K 14/00* (2006.01)
*C07K 1/16* (2006.01)
*C07K 1/18* (2006.01)

(52) U.S. Cl. .................. 530/350; 530/412; 530/416
(58) Field of Classification Search ............... 530/350, 530/417; 435/69.7, 514, 170
See application file for complete search history.

(56) References Cited

U.S. PATENT DOCUMENTS

| | | | |
|---|---|---|---|
| 3,625,833 | A | 12/1971 | Schaffer |
| 4,464,165 | A | 8/1984 | Pollard, Jr. |
| 4,617,266 | A | 10/1986 | Fahnestock |
| 4,699,783 | A | 10/1987 | Terman et al. |
| 4,801,687 | A | 1/1989 | Ngo |
| 5,075,423 | A | 12/1991 | Balint, Jr. |
| 5,100,788 | A * | 3/1992 | Lofdahl et al. ............ 435/69.7 |
| 5,151,350 | A | 9/1992 | Colbert et al. |
| 5,902,722 | A | 5/1999 | Di Cesare et al. |
| 6,555,661 | B1 | 4/2003 | Torres et al. |
| 2003/0166869 | A1 | 9/2003 | Vedantham et al. |
| 2005/0282294 | A1 | 12/2005 | Britsch |

FOREIGN PATENT DOCUMENTS

| | | |
|---|---|---|
| EP | 0 289 129 A2 | 11/1988 |
| EP | 0 124 374 B1 | 3/1989 |
| EP | 0 355 047 A | 2/1990 |
| JP | 61224997 | 10/1986 |

OTHER PUBLICATIONS

Trypticase Soy Agar Reference (2 pages).*
Fluka reference sheets (2 pages).*
Nout, M.J.R., et al., "Effect of Environmental Conditions During Soya-Bean Fermentation on the Growth of *Staphylococcus aureus* and Production and Thermal Stability of Entertoxins A and B," *International Journal of Food Microbiology* 7:299-309 (1988).
Beer, D. J., et al., "A Comparison of the Leakage of a Monoclonal Antibody From Various Immunoaffinity Chromatography Matrices," *Bioseparation*, 5(4): 241-247 (1995).
Charles, B. G., et al., "Cultivation of *Staphylococcus aureus* in a Synthetic Medium of Low Ultraviolet Absorptivity," *Antimicrobial Agents and Chemotherapy*, 10(6): 915-917 (1976).
Godfrey, M. A. J., et al., "A Sensitive Enzyme-Linked Immunosorbent Assay (Elisa) for the Detection of Staphylococcal Protein A (SPA) Present As a Trace Contaminant of Murine Immunoglobulins Purified on Immobilized Protein A," *Journal of Immunological Methods*, 149(1): 21-27 (1992).
Goldstein, I., et al., "Action of Group A Streptococcus Extracellular Product on the Connective Tissue of the Bovine Heart Valve," *Infection and Immunity*, 9(1): 20-26 (1974).
Good, R. A., et al., "Immunosuppressive Actions of Retroviruses," *Lymphology*, 23(2): 56-59 (1990).
Horenstein, A. L., et al., "Design and Scaleup of Downstream Processing of Monoclonal Antibodies For Cancer Therapy: From Research to Clinical Proof of Principle," *Journal of Immunological Methods*, 275(1-2): 99-112 (2003).
Merten, O. W., "Development of Serum-Free Media For Cell Growth and Production of Viruses/Viral Vaccines—Safety Issues of Animal Products Used in Serum-Free Media," *Developments in Biologicals*, 111: 233-257 (2002).
"Typical Analyses—Peptones and Hydrolysates," *BD Diagnostics*, 2004 Product Catalog: 34-35.
US 5,314,993, 05/1994, Love et al. (withdrawn)

* cited by examiner

*Primary Examiner*—Maryam Monshipouri
*Assistant Examiner*—Marsha Tsay (57) ABSTRACT

The invention relates to methods of producing Protein A without contamination of the Protein A by animal products. The invention also relates to a vegetarian fermentation media in which *Staphylococcus aureus* is grown to produce a vegetarian Protein A. The invention further relates to a vegetarian Protein A and the use of a vegetarian Protein A in therapeutic and prophylactic methods.

31 Claims, 5 Drawing Sheets

VEGETARIAN PROTEIN A PREPARATION AND METHODS THEREOF

BACKGROUND OF THE INVENTION

Protein A is a cell wall protein made by *Staphylococcus aureus*. The usefulness of Protein A stems from its ability to bind the Fc region of most mammalian immunoglobulin G (IgG) and, to a lesser extent, to immunoglobulin M (IgM) having a $V_{H3}$ region, without affecting immunoglobulin affinity for antigen. Protein A is used commercially to purify monoclonal antibodies that are often in turn used as therapeutics in human diseases like inflammatory diseases and cancer. Also, Protein A can itself be used as a therapeutic. Protein A can be administered to a patient in order to bind circulating immune complexes in autoimmune diseases like rheumatoid arthritis or to stimulate specific cytokine production in someone with an infection. In addition, when coupled to a chromatography resin, Protein A can act as a therapeutic absorber to treat plasma or whole blood by removing IgG complexes in disorders like autoimmune disease and transplant organ rejection.

Originally, Protein A was derived from the *S. aureus* cell wall, but bacterial strains which secrete the protein have been isolated and are also used to obtain Protein A. However, the preparation of Protein A by conventional methods presents a problem for its use in human therapeutics. *S. aureus* is grown in media that contains animal products as a source of amino acids for the bacteria. In particular, bovine hydrolysates and extracts are commonly used as supplements in bacterial growth media. Hence, obtaining Protein A from growth media containing animal-derived products leads to the possibility that animal products like prions, the causitive agent in Mad Cow, Scrapie and wasting disease, could be present in the media and transmitted to human patients. Protein A preparations can also be exposed to and contaminated with animal products during downstream purification processes. For example, in methods currently used, Protein A is purified using an IgG Sepharose chromatography column and the IgG coupled to the Sepharose chromatography column is typically of animal origin. However, the animal products that come to be associated with a Protein A preparation during the isolation and purification processes are not easily purified from the preparation by the methods presently known.

SUMMARY OF THE INVENTION

The present invention relates to a method of producing Protein A free of animal-derived product contamination by fermenting an *S. aureus* secretor strain in a media containing vegetarian amino acids or peptides instead of animal peptides, harvesting the Protein A-containing media and purifying the Protein A by applying it to a synthetic resin that lacks animal peptides and filtering the elutant from the resin.

In one embodiment of the method, the *S. aureus* secretor strain is *Staph aureus*, var *Imre* (*S. Imre*). In another embodiment of the invention, the Protein A is purified from the media using an anion exchange chromatography resin. In yet another embodiment of the invention, the Protein A eluted from the chromatography resin is further purified by hydroxyapatite or cationic exchange chromatography to remove non-proteineous contaminants. After purification, the Protein A can be concentrated and brought to physiological pH.

The present invention also relates to a vegetarian media for fermentation of the *S. aureus* that consists of yeast extract, vegetarian amino acids or peptides, glucose and essential salts. In one embodiment, the vegetarian amino acids or peptides are soy peptides. In addition, the invention relates to methods of producing a vegetarian Protein A, that is, a Protein A preparation free of animal product contamination, by growing the bacteria in the vegetarian media.

The invention further relates to a vegetarian Protein A preparation produced by the methods of the invention. The invention further relates to a pharmaceutical composition containing a vegetarian Protein A and a suitable carrier. In one embodiment, the pharmaceutical composition is used in a therapeutic method to treat a patient in need thereof. In particular, the pharmaceutical composition is used in a method to treat a patient in need of stimulation of cytokine or cryoglobulin production by administering the vegetarian Protein A pharmaceutical composition to the patient.

The invention also relates to the vegetarian Protein A immobilized to a chromatography resin to form a vegetarian Protein A-chromatography resin. In one embodiment, the vegetarian Protein A-chromatography resin is used in a method to bind antibodies or antibody fragments. In a particularly preferred embodiment, the vegetarian Protein A-chromatography resin is used to purify antibodies. The invention also relates to a pharmaceutical composition comprising the purified antibodies and a suitable carrier. In one embodiment, the pharmaceutical composition of purified antibodies is used to treat a patient in need thereof and, in a preferred embodiment, the antibodies are used to treat a patient having cancer.

The invention further relates to a pharmaceutical composition comprising the vegetarian Protein A-chromatography resin and a suitable carrier and methods in which the pharmaceutical composition is used to treat a patient in need thereof. In one embodiment of the method, the pharmaceutical composition is used to treat acquired hemophilia. In another embodiment, the pharmaceutical composition is used in a method to treat autoimmune diseases or immune-related problems. In a further embodiment of the method, the pharmaceutical composition is used to treat the autoimmune diseases rheumatoid arthritis or dilated cardiomyopathy. In yet another embodiment of the method, the pharmaceutical composition is used to treat the immune-related problem of graft-versus-host disease.

Thus, the invention provides for a method to produce Protein A in a manner as to prevent its contamination with animal proteins. Further, it advantageously provides for a Protein A preparation and Protein A pharmaceutical compositions that have not come in contact with animal products, ensuring that the Protein A is not contaminated by them. This is especially important for the use of Protein A in human therapeutics.

DETAILED DESCRIPTION OF THE INVENTION

A description of preferred embodiments of the invention follows. Protein A can be obtained from any Protein A-producing strain of *S. aureus* including those strains that are naturally-occurring, isolated or genetically engineered. Protein A-producing strains of *S. aureus* can also include those strains in which Protein A remains embedded in the cell wall and those strains that secrete Protein A into the growth media, preferably *S. aureus*, var *Imre*, for instance. Methods by which Protein A can be recovered from the *S. aureus* cell wall (e.g., enzyme digestion) are well-known by those with skill in the art. Protein A recovered in this manner can be purified to eliminate the digested cellular components. It is preferable, however, to obtain Protein A from *Staphylococcus* strains that secrete Protein A into the media such that it is only necessary to harvest the Protein A from the media.

Fermentation and Harvest *S. aureus* strains are fermented in conditioned media that lacks animal-derived peptides to prevent contamination of the Protein A by animal products. As referred to herein, "animal products" are defined as any material transmitted or derived from a non-human animal, the material including peptides, proteins, amino acids, protein-like materials, nucleic acids, viruses and the like. As referred to herein, the term "vegetarian Protein A" is defined as a Protein A composition uncontaminated by animal products or any animal-derived peptides that are derived from the fermentation media or the purification media. Similarly, the term "vegetarian media" refers to fermentation media uncontaminated by animal products or any animal-derived peptides. As used herein, the term "vegetarian amino acids or peptides" refers to any peptides, proteins, amino acids or protein-like materials that are not derived from a non-human animal.

Secretor bacteria can be fermented in any amount of vegetarian media sufficient to grow the bacteria and produce the desired amount of Protein A. Most preferably, the *S. aureus* are grown in a large scale manufacturing batch in fermentor tanks. Fermentation conditions (i.e., airflow, temperature, agitation, pH and pressure) can be controlled and/or monitored electronically, with, for example, a microprocessoror, or by any other electronic means. Some particularly preferred conditions include fermentation of the *S. aureus* at about 37° C. and an airflow of about 1 liter/minute of sterile air per liter of media. The media can consist of the components of conditioned media for *S. aureus* growth that are known in the art, typically, yeast extract, glucose and essential salts, and, in the case of the invention, includes vegetarian amino acids and peptides (e.g., soy, pea hydrolyzate or cotton seed hydrolyzate peptide) as a source of amino acids. Vegetarian amino acids or peptides could, for instance, be derived from any non-animal (e.g., plant or plant-like) or synthetic (e.g., chemically synthesized) source and in one embodiment of the invention, the vegetarian amino acids or peptides are derived from soy. The components can be at a concentration of about 50 grams/liter (g/L) yeast extract, 15 g/L soy peptides and 5 to 10 g/L glucose dissolved in purified, deionized water with diluted phosphoric acid and diluted sodium hydroxide added as needed during fermentation to control the pH at between about 7 and 8. The media can further contain at least 0.67 milliliters/liter (ML/L) of polyethylene glycol to prevent foaming in the fermentation mixture.

In a preferred embodiment the fermentation broth is inoculated with approximately $5\times10^9$ *S. aureus* of the *Staph Imre* strain for large batch manufacture. To ensure that the Protein A preparation is completely free of animal product contamination, the seed of *S. aureus* used to inoculate the fermentation broth is also maintained in vegetarian media. The *S. aureus* are preferably fermented for 13 to 14 hours at 37° C. to obtain a high density of bacteria at a concentration measuring greater than 50 at a wavelength of 560 nanometers (nm) (or greater than $5.2\times10^8$ *S. aureus*/mL), but can be fermented for anywhere from 10 to 24 hours to obtain a desired bacterial concentration, the appropriate growth time determined by one with skill in the art. Further testing to confirm the purity of the culture can be done by growing an aspectically collected sample of the fermentation broth on Mueller Hinton Agar (which favors gram negative bacteria growth) and, on simple metabolites such as glutamine, galactose, mellobiose or the like, identify a consistent pattern of growth or non-growth depending on the metabolite. Kits to perform such a identification and purity analysis are available commercially, for example, from BioMérieux.

The fermentation broth can be assessed visually under a microscope to ensure the broth is not contaminated with other microorganisms. Similarly, the *S. aureus* in the culture can be inspected using a microscope for the proper morphology which includes having: the shape of gram positive cocci, pleiomorphism (i.e., single colonies, chains or roseates) and a size of approximately 0.6 microns. The cultured *S. aureus* can also be assessed for quality and health by determining if they exhibit a round, raised, grayish morphology on blood agar plates, have an ability to cause the β-hemolysis of sheep blood after 48 hours and test positive for the enzymes coagulase and catalase.

The fermentation of the broth under the desired conditions will preferably result in the production of vegetarian Protein A to a concentration of 0.68 milligrams/milliliter (mg/mL) of media. The vegetarian Protein A in the fermentation media can then be harvested by passing the broth through a filtration system (for example, Millipore Prostak filtration system) using 0.1 micron filters. Other suitable filtration methods can also be employed to remove bacterial cells, for instance, any method of depth filtration with media aids, such as diatomaceous earth. The *Staphylococcus* cells can also be eliminated by continuous high speed centrifugation of the *S. aureus* fermentation media, the centrifugation pelleting the bacterial cells and enriching the media with the secreted Protein A. The cell-free broth can then be passed through a sterile 0.22 micron filter or the like before further purification.

Purification

The vegetarian Protein A undergoes several downstream processing steps to produce a purified vegetarian Protein A preparation. Thus, the methods of the invention also relate to the purification of the vegetarian Protein A. In one embodiment, the vegetarian Protein A-containing media can undergo dialfiltration to decrease the conductivity of the solution and remove non-proteinacious material that co-exists with vegetarian Protein A. The conductivity of the vegetarian Proetin A solution is preferably reduced such that it is no more than 2 milliSiemens/centimeter (mS/cm). In one embodiment, the vegetarian Protein A solution is diafiltered in 10 millimolar (mM) TrisHCl and NaCl. Diafiltration of the solution can be performed using a filter and the desired buffer and, in an embodiment of the invention, is done using a 10,000 molecular weight cut off (MWCO) membrane in 10 millimolar (mM) TrisHCl buffer at pH 7.8. Methods of diafiltration are known in the art and can include both MWCO membranes (e.g., Millipore PROCON), a hollow fiber dialysis filter (e.g., Fresenius Optiflux) or any other filtration system with a molecular weight cut off appropriate to achieve the maximum and/or desired yield of vegetarian Protein A.

The vegetarian Protein A-containing media can then be purified using a chromatography method in which the chromatographic materials are free of animal-derived products. In one embodiment of the invention, Protein A is purified by applying the vegetarian Protein A-containing solution to an anion-exchange chromatography resin. A variety of anion-exchange resins can be employed and suitable matrices include cellulose, acrylamide and silica gel. Many anion exchange chromatography systems are commercially available and, in the most preferred embodiment of the invention, the vegetarian Protein A-containing solution is purified using the MacroPrep High Q anion exchange resin. Protein A can be applied to the anion exchange chromatography matrix by methods well-known in the art. Typically, the chromatography column is equilibrated to the pH and conductivity of the vegetarian Protein A-containing solution (i.e., pH 7.5 to 8.5) and the vegetarian Protein A-containing media is passaged over the column which binds the vegetarian Protein A due to intermolecular interactions. In one embodiment, the vegetarian Protein A bound to the column is washed with equilibration buffer and can be washed with any buffer at the appropriate pH and conductivity. The chromatography is preferably performed at about a 5.7 to 7.9 cm/minute flow rate on a column having a height of about 24 centimeters. The vegetarian Protein A can then be eluted from the column using the appropriately charged buffer and, in a particular embodiment of the invention, using 20 mM TrisHCl and sodium chloride (NaCl) having a conductivity of about 18 mS/cm. In one embodiment of the invention, anion exchange chromatography of the vegetarian Protein A media produces a vegetarian Protein A eluant that contains an at least 95% pure Protein A. In a preferred embodiment, the Protein A eluant contains Protein A at a purity of greater than 95% and most preferably, at a purity of 97 to 99%.

In another embodiment of the invention the vegetarian Protein A elutant from the anion exchange chromatography column is diafiltered to adjust the pH and conductivity of the solution. The diafiltration is most preferably performed using a 10,000 MWCO membrane to produce a vegetarian Protein A filtrate having a pH of about 6.5 to 7.1 and a conductivity of about 1 to 2 mS/cm.

In yet another embodiment of the invention, the vegetarian Protein A filtrate can then optionally be further purified by hydroxyapatite chromatography to remove non-protein contaminants. Hydroxyapatite is a mixed-mode ion-exchange chromatography resin that causes proteins (e.g., Protein A) to elute early and carbohydrate-containing compounds to elute subsequent to the proteins. It is preferred that the hydroxyapatite resin have a resin bed height of about 20 cm in a chromatography column. Once the vegetarian Protein A filtrate is applied to the hydroxyapatite resin, it is washed with a buffer and, in an embodiment of the invention, the buffer is 14 mM sodium phosphate at pH 6.8. In a preferred embodiment, the vegetarian Protein A is then eluted from the hydroxyapatite column using 370 mM sodium phosphate at pH 6.8.

After purification the vegetarian Protein A can be concentrated to a desired volume and/or concentration appropriate for storage or use. Mechanisms to concentrate proteins are well-known in the art and typically involve filters or centrifugation. In one embodiment of the invention, the vegetarian Protein A solution is concentrated after the anion exchange chromatography, while in another embodiment the vegetarian Protein A solution is concentrated after the hydroxyapatite chromatography. The vegetarian Protein A eluant can be concentrated using a 10,000 MWCO filter to achieve a 5 to 20 mg/mL vegetarian Protein A preparation in a preferred embodiment of the invention. In order to use the vegetarian Protein A in applications in which physiological pH is required, the pH of the concentrated vegetarian Protein A can be adjusted to neutral pH, preferably using phosphate buffer.

Compositions and Methods of Treatment

The invention further relates to a vegetarian protein A produced by the methods of the invention. The vegetarian Protein A can be administered directly to patients or, more preferably, combined with a suitable carrier. Hence, the invention also relates to a pharmaceutical composition comprising the vegetarian Protein A and a suitable carrier. Suitable pharmaceutical carriers (e.g., Eupergit or Glyoxal agarose beads) are known in the art and vary according to the route of administration.

The invention further relates to methods of treating a patient with vegetarian Protein A pharmaceutical compositions. In one embodiment, a patient in need thereof is administered a vegetarian Protein A pharmaceutical composition. In another embodiment, the patient is administered a vegetarian Protein A pharmaceutical composition in order to stimulate cytokine or cryoglobulin production. Most preferably, the patient is treated in this manner to fight an infection or enhance a compromised immune system. The vegetarian Protein A pharmaceutical composition is administered as appropriate as determined by one with skill in the art, but a more suitable method of administration is by injection into the patient's bloodstream.

The invention also relates to vegetarian Protein A immobilized to a chromatography resin. The resin to which vegetarian Protein A is immobilized can be as small as 40 microns or as large as 300 microns. In one embodiment of the invention, the resin is a synthetic polymer (e.g., polymethacrylate), semi-synthetic polymer (e.g., polygalactose) or amorphous material (e.g., diatomaceous earth or silica). In a further embodiment of the invention, the vegetarian Protein A-resin can be produced by reacting a carboxyl or amino group on the vegetarian Protein A with a chemically functional group on the chromatography resin. In a preferred embodiment of the invention, carboxyl groups of the vegetarian Protein A are reacted with amino groups on the resin to produce the vegetarian Protein A-resin. In another embodiment, the resin can be activated with triazine and the Protein A reacted with the triazine bound to the resin. In still another embodiment, very high titers of Protein A binding can be achieved with aldehyde activated media or carbohydrate media by first oxidizing the resin with sodium periodate, followed by reduction of the Protein A on the media using ascorbate or sodium borohydrate. In the most preferred embodiment, the vegetarian Protein A is attached to the resin at multiple places in the protein to minimize leaching of the Protein A from the resin.

The invention also relates to a method of binding antibodies or antibody fragments to the vegetarian Protein A-resin. The terms "antibody" and "antibody fragments" are intended to encompass both polyclonal and monoclonal antibodies. In addition, the term antibody as used herein also encompasses various types of antibodies, including human, chimeric, humanized, primatized, veneered or single chain antibodies. The antibodies or antibody fragments can be bound to a vegetarian Protein A-resin by applying the antibodies or antibody fragments to the vegetarian Protein A-resin by methods well-known in the art. For example, antibodies are typically bound to the resin by applying an antibody solution to the resin under conditions such that the antibodies bind the resin and washing the antibody-bound resin with the appropriate buffer to remove unbound material. In one embodiment, the antibodies or antibody fragments are bound to the vegetarian Protein A-resin in order to purify the antibodies.

The invention further relates to a pharmaceutical composition comprising antibodies or antibody fragments purified using the vegetarian Protein A-resin and a suitable carrier (e.g., Dohkai MicroSphere silicia beads). Antibodies can be purified by methods well-known to one with skill in the art. In fact, purification of antibodies using a Protein A-chromatography resin is one of the most widely used methods to do so and the methods are well-known in the art (see, for example, Harlow, E. and Lane, D. P., Antibodies, Cold Spring Harbor Laboratory, Cold Spring Harbor, N.Y. (1988)). The invention further relates to treating a patient in need thereof with a pharmaceutical composition of the purified antibodies or antibody fragments in a suitable carrier. There are many diseases in which purified antibodies can be used as a treatment including inflammatory disease (e.g., Crohn's disease, Behcet's disease and colitis), rheumatic disease, multiple sclerosis, Alzheimer's disease, Lupus, cancer, skin disorders and allergy. In a particular embodiment of the invention, the patient is treated for cancer.

The invention also relates to a pharmaceutical composition comprising the vegetarian Protein A-resin and a suitable carrier and methods of treating a patient in need thereof by administering the vegetarian Protein A-resin pharmaceutical composition. In one embodiment of the method, the patient is treated for acquired hemophilia. In another embodiment of the invention the patient is treated for autoimmune disease or immune-related problems. In a further embodiment of the invention, the autoimmune disease is rheumatoid arthritis or dilated cardiomyopathy. In yet another embodiment of the invention, the immune-related problem is graft-versus-host disease or rejection of transplanted organs.

Suitable Carriers and Modes of Administration

According to the methods, pharmaceutical vegetarian Protein A compositions or purified antibodies or antibody fragments can be administered to a patient by an appropriate route, either alone or in combination with another drug. An effective amount of a pharmaceutical composition (e.g., vegetarian Protein A, vegetarian Protein A immobilized to a chromatography resin or antibodies purified using a vegetarian Protein A-resin) is administered to a patient. An effective amount is an amount sufficient to achieve the desired therapeutic or prophylactic effect, under the conditions of administration, such as an amount sufficient to stimulate immune cells or bind disease-related proteins. The pharmaceutical compositions can be administered in a single dose or in multiple doses to ensure the patient sustains high plasma levels of the vegetarian Protein A pharmaceutical compositions or antibodies purified by vegetarian Protein A during therapy. The dosage can be determined by methods known in the art and is dependent, for example, upon the particular agent chosen, the subject's age, body weight, sensitivity and tolerance to drugs, and overall well-being. Suitable dosages for pharmaceutical compositions comprising vegetarian Protein A can be about 0.001 milligrams/kilogram (mg/kg) to about 10 mg/kg body weight per treatment and for antibodies purified using vegetarian Protein A about 0.01 mg/kg to about 100 mg/kg body weight per treatment.

A variety of routes of administration are possible including, for example, oral, dietary, topical, transdermal, rectal, parenteral (e.g., intravenous, intraaterial, intramuscular, subcutaneous injecton, intradermal injection), and inhalation (e.g., intrabonchial, intranasal or oral inhalation, intranasal drops) routes of administration, depending on the agent and disease or condition to be treated. Administration can be local or systemic as indicated. The preferred mode of administration can vary depending on the particular agent chosen, and the particular disease being treated; however, oral or parenteral administration is generally preferred.

Formulations of vegetarian Protein A pharmaceutical compositions and purified antibodies will vary according to the route of administration selected (e.g., solution, emulsion or capsule). Suitable pharmaceutical carriers can contain inert ingredients which do not interact with the vegetarian Protein A pharmaceutical compositions or the vegetarian Protein A-purified antibodies. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's lactate and the like. Methods of encapsulation compositions (such as in a coating of hard gelatin or cyclodextran) are known in the art. For inhalation, the agent can be solubilized and loaded into a suitable dispenser for administration (e.g., an atomizer or nebulizer or pressurized aerosol dispenser).

The following examples are offered by way of illustration of the invention and not meant to limit the invention in any way.

EXEMPLIFICATION

Example 1

The components of the fermentation broth in which the *S. aureus* were cultured to produce vegetarian Protein A were at about a concentration of 50 grams/liter yeast extract, 15 grams/liter soy peptides and 5 to 10 grams/liter glucose. In particular, for manufacturing batch fermentation, the vegetarian media contained the materials at the concentrations identified in Table 1.

TABLE 1

Materials for the Fermentation Broth.

| Description | Amount Required |
|---|---|
| Soytone | 6.75 ± 0.2 kg |
| Sodium Chloride | 1.875 ± 0.2 kg |
| Glucose | 0.938 ± 0.1 kg |
| Potassium Monobasic Phosphate | 0.938 ± 0.1 kg |
| Yeast Extract | 18.75 ± 0.4 kg |
| Polyethylene Glycol P-2000 Anti-foam | 250 ± 5 mL |
| *Staphylococcus aureus*, var. IMRÉ "vegan working seed" | 1 vial ($5 \times 10^9$) |
| Phosphoric Acid, N.F. | as needed to maintain pH 7 to 8 |

TABLE 1-continued

Materials for the Fermentation Broth.

| Description | Amount Required |
|---|---|
| Undiluted Sodium Hydroxide, 50%, Undiluted | as needed to maintain pH 7 to 8 |

Example 2

Conditions for the fermentation of vegetarian Protein A-producing S. aureus in manufacturing batch fermentation are listed in Table 2.

TABLE 2

Fermentor Parameters

| Control System | Temp. | Airflow | Pressure | Agitation | pH |
|---|---|---|---|---|---|
| Specification | 37 ± 1° C. | 325 ± 25 sLpm | 6.0 ± 1 psig | 400 ± 25 rpm | 8.0 ± 0.5 |

Example 3

Vegetarian Protein A Activity Testing

The activity and yield of Protein A at each stage was determined by using a simple assay. A small IgG-Sepharose column was verified for binding activity and binding capacity using Protein A produced by standard methods. A sample containing a sub-saturating amount of Protein A was applied, the column washed, the Protein A eluted with pH 2.2 glycine buffer and the concentration of Protein A determined by $OD_{275}$. This assay was used throughout to determine vegetarian Protein A activity and yield. Alternatively, all but crude extracts can be more conveniently quantitated using HPLC and reverse phase, ion exchange or size exclusion column chromatography.

MacroPrep High Q Anion Exchange Chromatography

After evaluating a variety of commercially available chromatography resins (Mallinckrodt, EMD, BioRad, Millipore), BioRad MacroPrep High Q(uarternary) anion exchange chromatography resin was selected. Diafiltered broth was applied to a small 67 mL column using a Pharmacia Biotech BioPilot automated chromatography system using Unicorn Software for configuration management (1.5 cm ×38 cm column; 12 mL/min) and data collection. After applying the diafiltered broth, the column was washed with 6 column volumes of 10 mM TrisHCl pH 7.8. The active vegetarian Protein A was eluted using 6 column volumes with 20 mM TrisHCl pH 7.8 +NaCl to 8 mS/cm (step gradient). The column was subsequently washed with 20 mM TrisHCl pH 7.8+0.5 M NaCl to remove brown material that adhered to the upper half of the column. Periodically, the column can be totally stripped by using several column volumes of 0.1 M NaOH followed by washing with several column volumes of 0.2 M TrisHCl pH 7.8 to adjust the pH and 10 mM TrisHCl to adjust the conductivity.

Approximately 0.5 grams (gm) of protein in 150 mL of diafiltered/concentrated broth was applied to a 67 mL column containing 106 mg of vegetarian Protein A. In the fractions selected (cut), 58 mg vegetarian Protein A were recovered (55%). Approximately 28 mg of vegetarian Protein A were contained in other fractions available (26%). While only the first cut was explored extensively, the SDS-PAGE suggested that later fractions might also be suitable. If total elution cut is possible, the recovery would then be 81% for the anion exchange chromatography step.

FIG. 1 shows the SDS-PAGE performed on cell free broth, diafiltered broth, the MacroPrep Q flow through, and various fractions obtained from the MacroPrep High Q chromatography run. No attempt was made to adjust load amounts so several of the lanes were overloaded for one or more bands. Despite the saturation of several bands, some interesting observations can still be made. The profile analysis suggested that vegetarian Protein A could account for as much as 20% of the protein present in the broth. (No attempt was made to determine the amount of lipid or carbohydrate present even though there was indirect chemical evidence of both.) Second, some of the proteins evident in the broth did not bind to the MacroPrep Q and passed through the column (see column flow through).

Fractions 5 through 11 were diluted and applied to SDS-PAGE Novex 4 to 12% gradient gel. Previous studies have demonstrated a linear response from 0.05 microgram (μg) to 2.0 μg samples using this system. Several minor bands were evident under the main band. This is typical of Protein A and represents isoforms that other studies have demonstrated to be present in fermentation products. The presence of the isoforms is not due to degradation occurring in the downstream purification process but, instead, is likely due to degradation during the fermentation process as proteases are well-known to be secreted by *S. aureus*. A band scan (more accurate) as opposed to a line scan of Fraction 6 is presented in FIG. 2. The main peak accounts for 90.2% of the protein with isoforms accounting for an additional 8.4%. Fraction 7 (profile not shown) had a main peak of 96.5% and isoforms of 1.9%. Fraction 8 (profile not shown) had a main peak of 97.4% and isoforms of 1.0%.

Evidence that the bands designated as isoforms had Protein A activity was determined by performance of a western blot for Protein A activity which is presented in FIG. 3. One hundred nanograms (ng) and 10 ng of a pooled sample of MacroPrep Q prepared vegetarian Protein A in duplicate was run on a Novex SDS-PAGE 4 to 12% gel. Pre-stained molecular weight standards were included on the gel. When the gel electrophoresis was complete, the protein samples were electrophoretically (60V/300 mAmp/1 hr) transferred to a 0.2 micron nitrocellulose membrane (Bio-Rad) in Towbin transfer buffer. The blotted membrane was washed in TrisHCl buffered saline and then blocked for 1 hour using SuperBlock. After a wash with 0.05% Tween-20 in TrisHCl buffer saline (TTBS), the membrane was incubated with a rabbit anti-mouse IgG-Alkaline Phosphatase conjugate for 30 minutes. After two 5 minute washes in TTBS the membrane was immersed in Vector Black stain from Vector Labs (BCIP/NBT Substrate Kit, 5-bromo-4-chloro-3-indolyl phosphate/nitroblue tetrazolium). The by-product of the reactions of the substrates with alkaline phosphatase forms as a black precipitate in the membrane as the chemical reaction proceeds and the position of alkaline phosphatase can be identified. Since the alkaline phosphatase was conjugated to rabbit IgG, its position identified the position of Protein A activity on the membrane.

Not only was the main band of vegetarian Protein A and Protein A prepared by standard methods (see Fresenius SpA, FIG. 3) readily stained using this technique, several minor bands were readily evident just below the main band. Furthermore, the main band of vegetarian Protein A ran between the 50,000 kilodalton (KD) and the 38,000 KD molecular weight markers. Protein A prepared by standard methods has a molecular weight of 47,000 KD as determined by MALDI TOF mass spectrometry. Thus, the Western blot confirmed that the vegetarian Protein A was of the expected size.

Example 4

Ceramic HydroxyApatite Type 1

Pooled fractions of MacroPrep Q were diafiltered to less than 2 mS/cm with 14 mM Sodium Phosphate (Na Phosphate) at pH 6.8. The sample was applied to an 8 mL BioRad Ceramic HydroxyApatite chromatography column equilibrated with 14 mM Na Phosphate. A shallow peak appeared during the flow through. (The BioPilot uses a UV band width filter from approximately 260 to 290 nanometers.) Since the peak was shallow, it likely represented an artifact of buffer carry over or some other buffer condition, though it could represent a real material. The column was then washed with 5 column volumes of 14 mM Na Phosphate pH 6.8 (1.7 mS/cm). Then the vegetarian Protein A was eluted with 5 column volumes of 370 mM Na Phosphate pH 6.8 (25 mS/cm).

Figure 4:
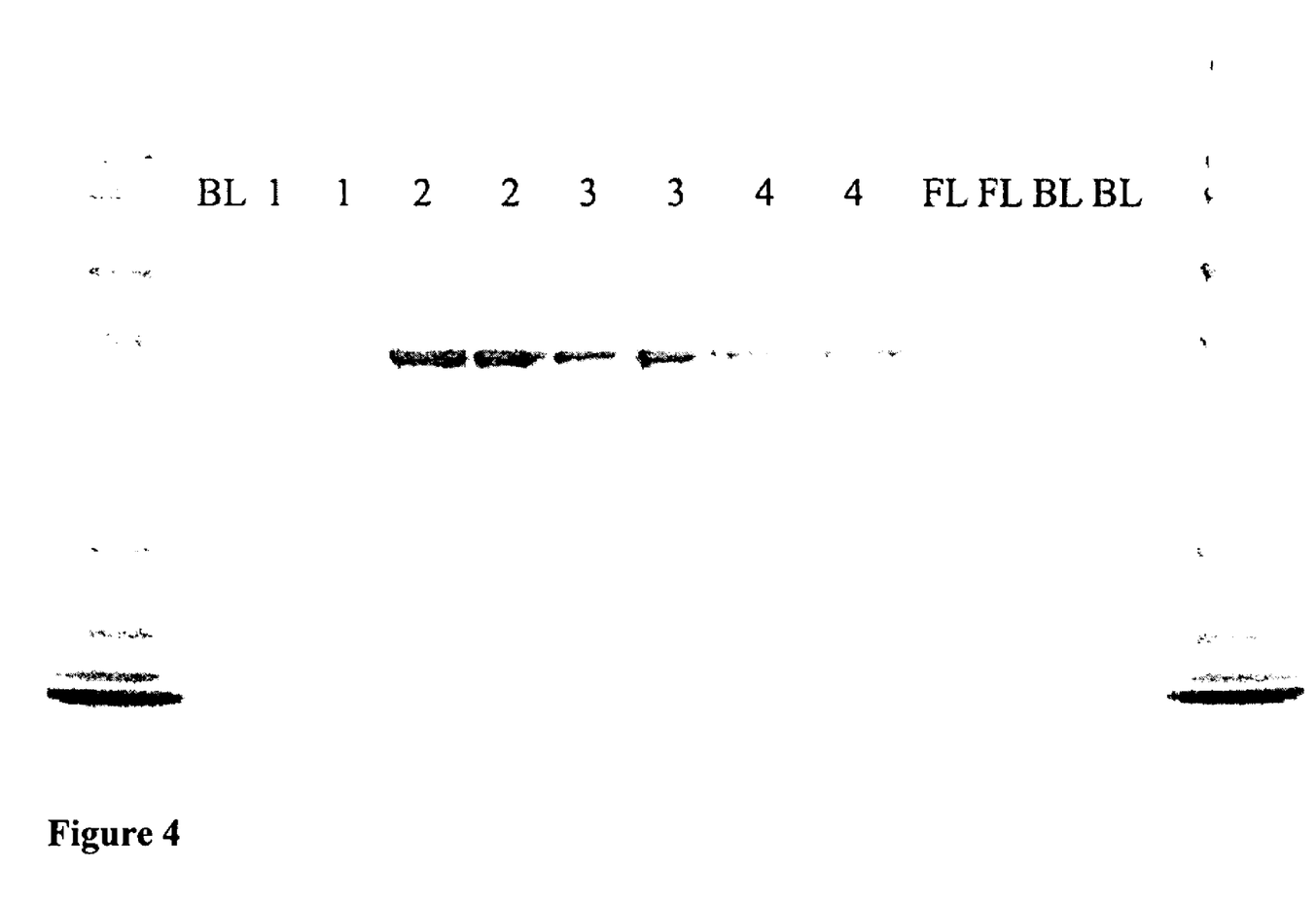
FIG. 4 is an SDS-PAGE gel illustrating the fractions from vegetarian Protein A eluted from a ceramic hydroxyapatite column.

First, the column was loaded with 26 mg of vegetarian Protein A, as determined by the activity assay, and 27 mg of active vegetarian Protein A were recovered, i.e., there was complete recovery within the error of the assay. Samples of the main peak were run diluted or undiluted, as appropriate for appropriate loading, on a NOVEX 4 to 12% SDS-PAGE (see FIG. 4). Once again there was one main band with several minor bands just below the main vegetarian Protein A band. A minor band was also evident near the bottom of the gel near the dye front.

Figure 1:
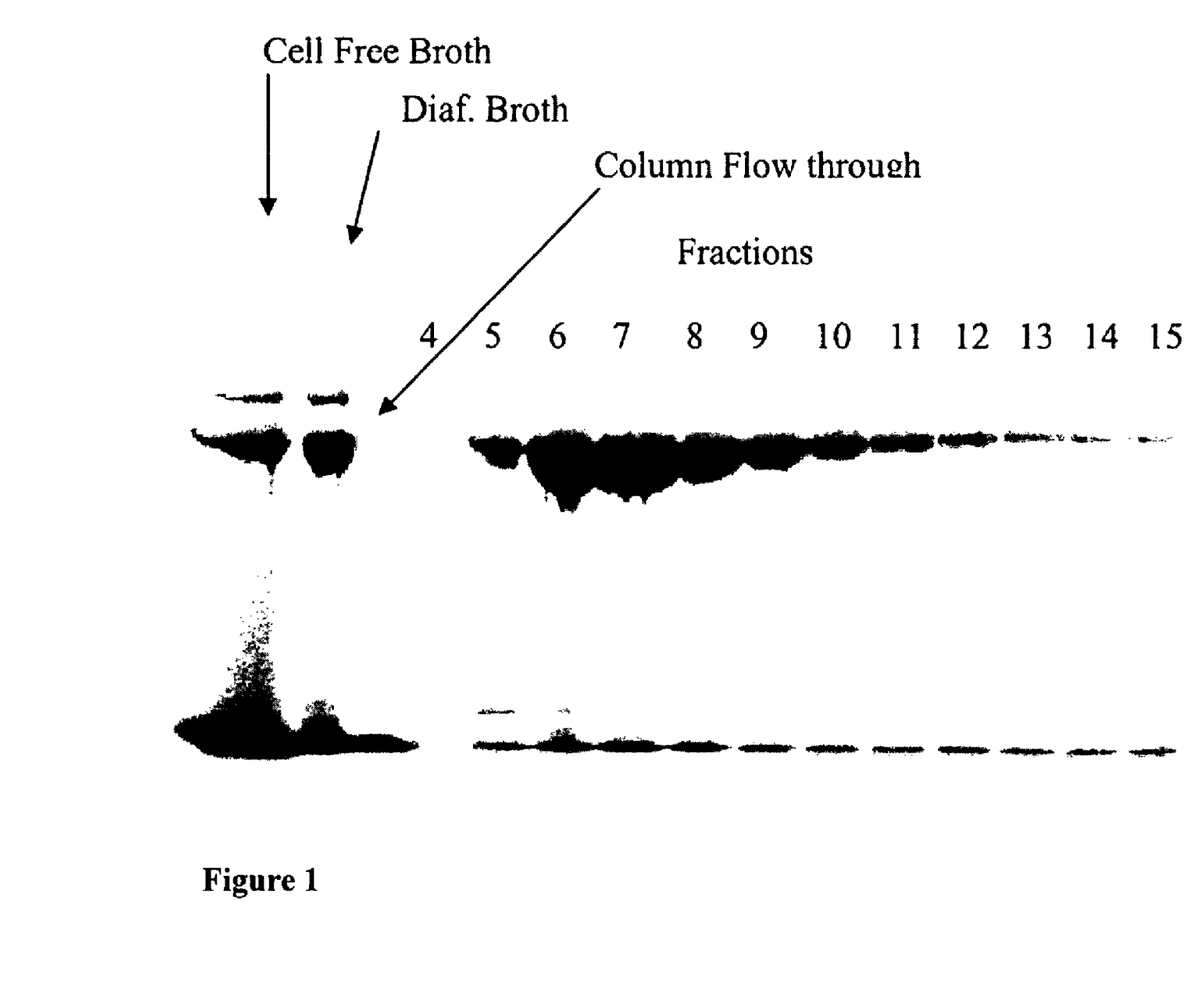
FIG. 1 is an SDS-PAGE gel illustrating the fractions obtained from vegetarian Protein A eluted from a MacroPrep High Q anion exchange column.
Figure 2:
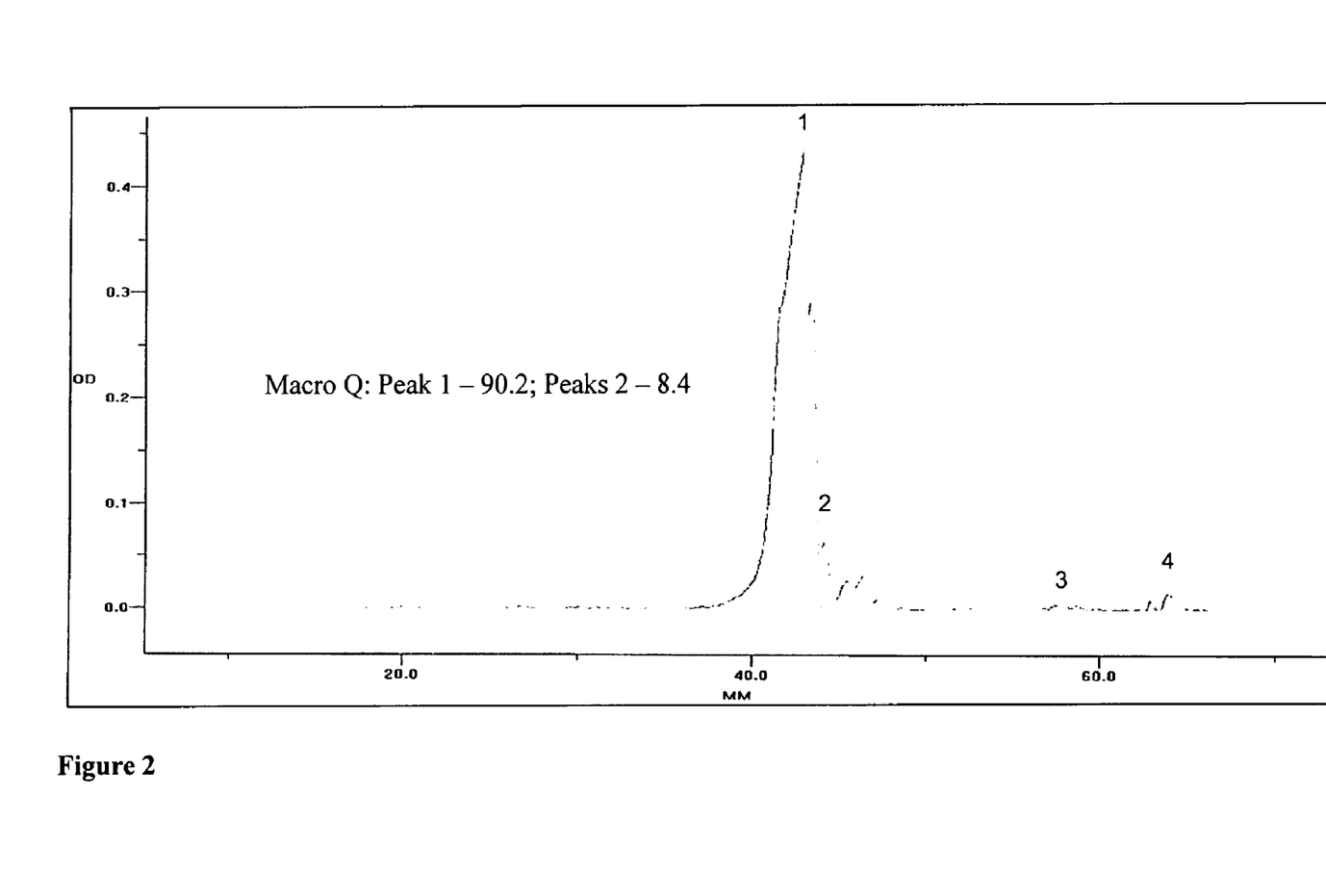
FIG. 2 is a linear chromatographic profile illustrating fraction 6 from vegetarian Protein A eluted from a Macro-Prep High Q anion exchange column.
Figure 3:
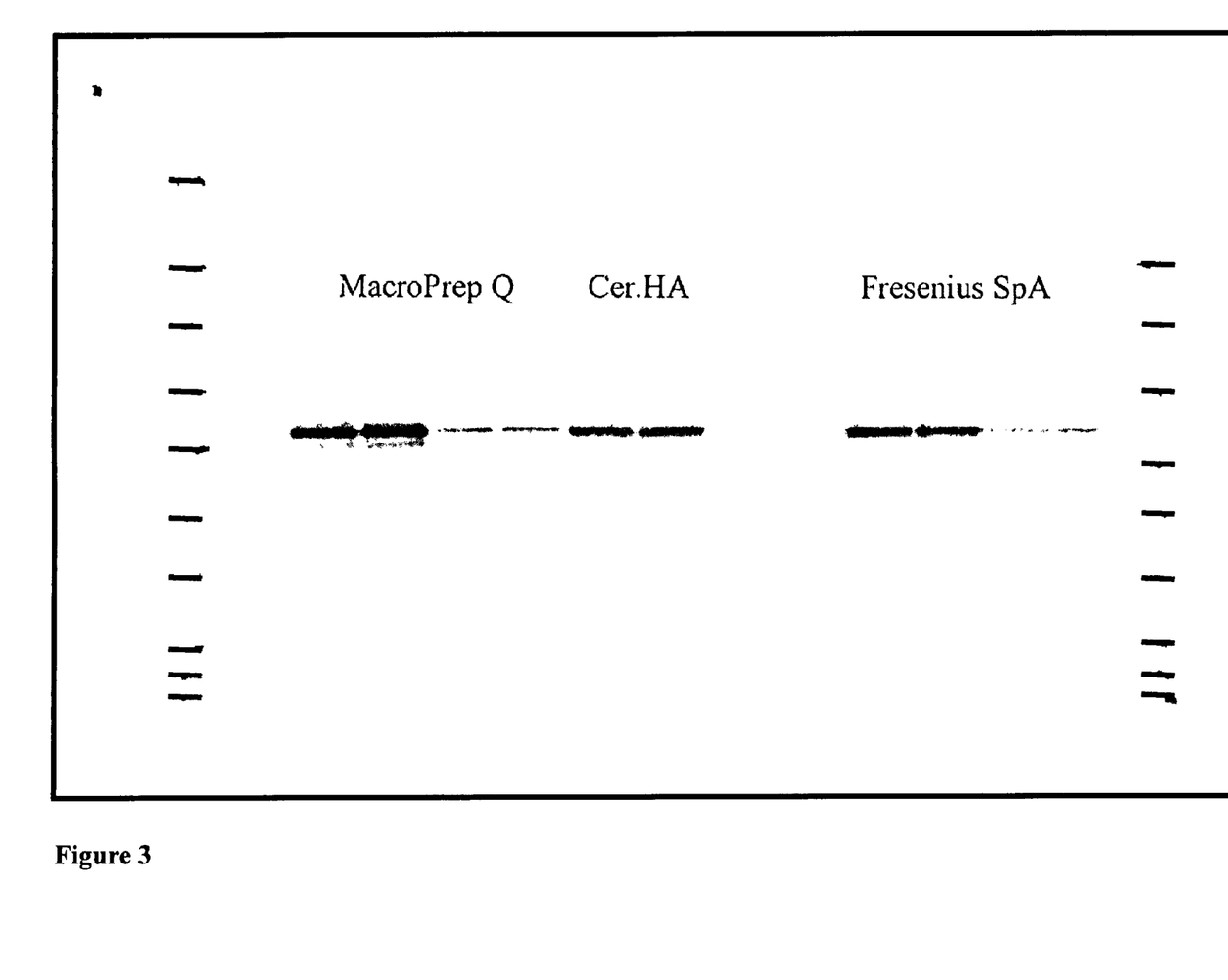
FIG. 3 is a western blot illustrating the activity of vegetarian Protein A purified by MacroPrep High Q anion exchange chromatography compared to that of a standard Protein A preparation.
Figure 5:
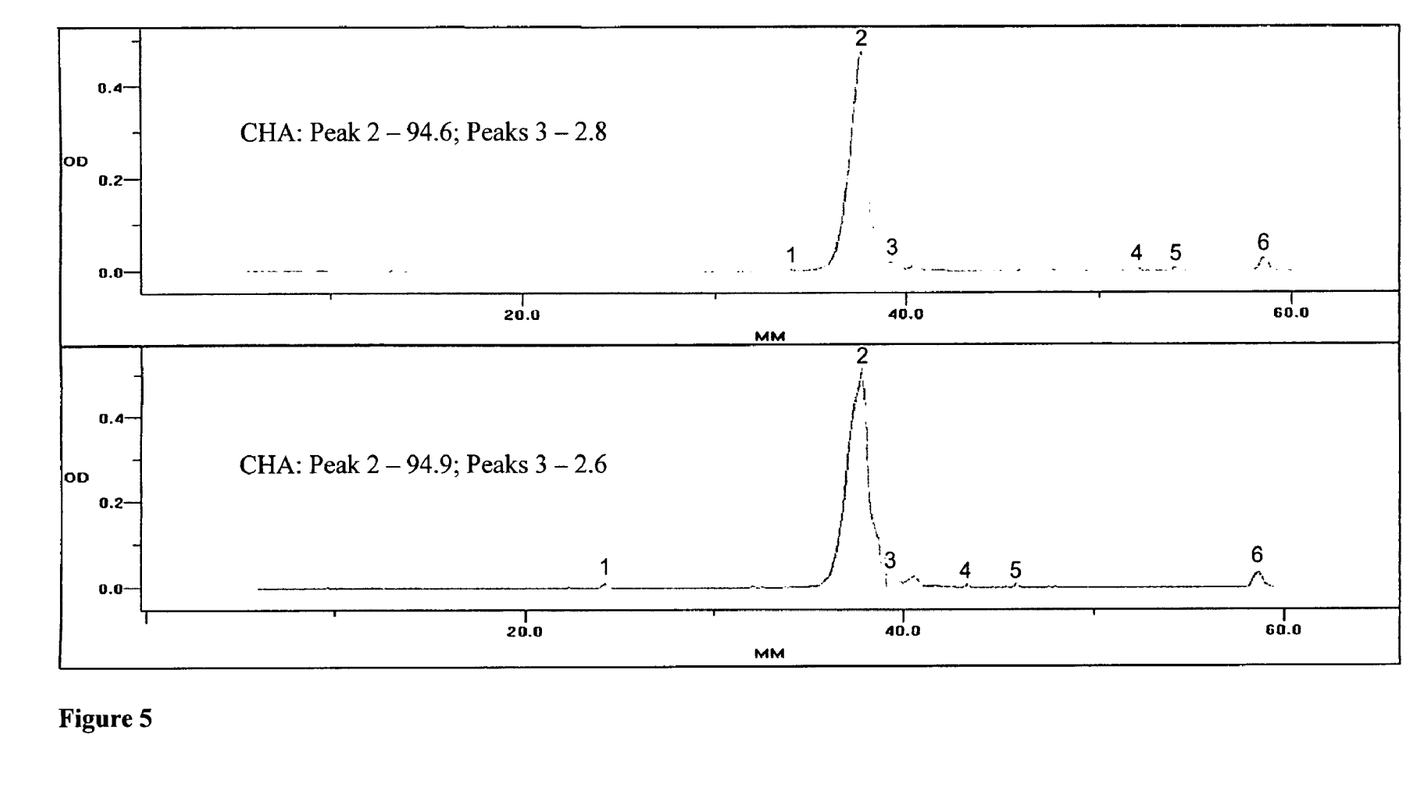
FIG. 5 is the linear chromatographic profiles illustrating the content of each band of fraction 3 from the vegetarian Protein A eluted from a ceramic hydroxyapatite column.

A sample of Fraction 2 was tested for Protein A activity by western blot. The main band and isoforms were readily evident as seen in FIG. 3. No other Protein A activity was evident on the western blot. In FIG. 5, a profile analysis was performed on each of the bands of Fraction 3 on the SDS-PAGE. The main band of each profile represented 94.9% and 94.6% of the protein present. The isoforms represented 2.8% and 2.6%, respectively. Thus, vegetarian Protein A represented approximately 97% to 98% of the protein present.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for producing vegetarian Protein A comprising:
    fermenting a secretor strain of *Staphylococcus aureus* (*S. aureus*) in a media containing yeast extract, vegetarian amino acids and peptides, glucose, and essential salts, said media being free of animal product, to produce a Protein A-containing media;
    harvesting the Protein A-containing media; and
    purifying the vegetarian Protein A by applying the Protein A-containing media to a synthetic anion exchange chromatography resin lacking animal products and eluting the Protein A from the resin followed by contacting with a ceramic hydroxyapatite chromatography column and eluting the Protein A from the column.

2. The method of claim 1 wherein the *S. aureus* is the secretor strain Staph Imre.

3. The method of claim 2 wherein the *S. aureus* are fermented for 10 to 24 hours.

4. The method of claim 3 wherein the *S. aureus* are fermented for 13 to 14 hours.

5. The method of claim 4 wherein the pH of the Protein A-containing media is adjusted to about 7.5 to 8.5 and the conductivity adjusted to less than 2 milliSiemens/centimeter by diafiltration using 10 millimolar TrisHCl and NaCl.

6. The method of claim 5 wherein the anion exchange chromatography is performed at about a 5.7 to 7.9 centimeter/minute flow rate on a column about 24 centimeters high.

7. The method of claim 6 wherein the Protein A is eluted from the chromatography column using at least 20 millimolar TrisHCl and NaCl at a conductivity of about 8 milliSiemens/centimeter.

8. The method of claim 7 wherein the pH of the Protein A elutant is adjusted to about pH 6.5 to 7.1 and a conductivity of about 1 to 2 milli-Siemens/centimeter by diafiltration with 14 millimolar sodium phosphate at pH 6.8.

9. The method of claim 8 wherein the Protein A is diafiltered using a membrane having 10,000 molecular weight cut-off point.

10. The method of claim 9 further comprising concentrating the Protein A filtrate to about 5 to 20 milligrams/milliliter using a 10,000 molecular weight filter and adjusting the Protein A solution to a neutral pH.

11. The method of claim 8 wherein the pH of the Protein A solution is adjusted to neutral pH using a phosphate buffer.

12. The method of claim 9 wherein the Protein A aplied to the hydroxyapatite chromatography column is washed with 14 millimolar sodium phosphate at pH 6.8 and eluted with about 370 mM sodium phosphate at pH 6.8.

13. The method of claim 12 wherein the height of the resin bed in the hydroxyapatite chromatoQraphy column is about 20 centimeters.

14. The method of claim 13 further comprising concentrating the Protein A elutant from the hydroxyapatite chromatography column to about 5 to 20 milligrams/milliliter using a 10,000 molecular weight filter and adjusting the Protein A solution to a neutral pH.

15. The method of claim 14 wherein the pH of the Protein A solution is adjusted to neutral pH using a phosphate buffer.

16. A method for producing vegetarian Protein A comprising:
    fermenting Staph Imre in a media consisting essentially of yeast extract, soy peptides, glucose and essential salts, to produce a Protein A-containing media;
    harvesting the Protein A-containing media;
    purifying the Protein A by applying the Protein A-containing media to an anion exchange resin lacking animal products and eluting the Protein A from the resin.

17. The method of claim 16 wherein a Staph Imre seed used to inoculate a fermenter is maintained in vegetarian media.

18. The method of claim 17 wherein the Staph Imre are fermented for 10 to 24 hours.

19. The method of claim 16 wherein the Staph Imre are fermented for 13 to 14 hours.

20. The method of claim 19 wherein the pH of the Protein A-containing media is adjusted to about 7.5 to 8.5 and the conductivity adjusted to about less than 2.0 milliSiemens/centimeter using 10 millimolar TrisHCl and NaCl.

21. The method of claim 20 wherein the anion exchange chromatography is performed at about a 5.7 to 7.9 centimeter/minute flow rate on a column about 24 centimeters high.

22. The method of claim 21 wherein the Protein A is eluted from the chromatography column using at least 20 millimolar TrisHCl and NaCl at a conductivity of about 18 milliSiemens/centimeter.

23. The method of claim 22 wherein the pH of the Protein A elutant is adjusted to about pH 6.5 to 7.1 and conductivity of about 1.0 to 2.0 milliSiemens/centimeter by diafiltration with 14 millimolar sodium phosphate at pH 6.8.

24. The method of claim 23 wherein the Protein A elutant is diafiltered using a membrane having a 10,000 molecular weight cut-off point.

25. The method of claim 24 further comprising concentrating the Protein A filtrate to about 5 to 20 milligrams/milliliter using a 10,000 molecular weight filter and adjusting the Protein A solution to a neutral pH.

26. The method of claim 25 wherein the pH of the Protein A solution is adjusted to neutral pH using a phosphate buffer.

27. The method of claim 24 further comprising applying the Protein A filtrate to a hydroxyapatite chromatography column to remove non-protein contaminants and eluting the Protein A from the hydroxyapatite chromatography column.

28. The method of claim 27 wherein the Protein A filtrate applied to the hydroxyapatite chromatography column is washed with 14 millimolar sodium phosphate at pH 6.8 and eluted with about 370 mM sodium phosphate at pH 6.8.

29. The method of claim 28 wherein the height of the resin bed in the hydroxyapatite chromatography column is about 20 centimeters.

30. The method of claim 28 further comprising concentrating the Protein A eluant from the hydroxyapatite chromatography column to about 5 to 20 milligrams/milliliter using a 10,000 molecular weight cut-off filter and adjusting the Protein A solution to a neutral pH.

31. The method of claim 30 wherein the pH of the Protein A solution is adjusted to neutral pH using a phosphate buffer.

* * * * *